United States Patent

Welland

[11] 4,111,643
[45] Sep. 5, 1978

[54] VENT CONTROL FOR A THERMAL SYSTEM

[75] Inventor: John M. Welland, Westport, Conn.

[73] Assignee: The Perkin-Elmer Corporation, Norwalk, Conn.

[21] Appl. No.: 772,160

[22] Filed: Feb. 25, 1977

[51] Int. Cl.² .................. 432 36; F27D 19/00; F26B 21/06
[52] U.S. Cl. ...................... 432/48; 34/46; 432/36
[58] Field of Search .................. 432/36, 48; 34/46; 210/31 R; 236/15 BF; 55/197

[56] References Cited

U.S. PATENT DOCUMENTS

| | | | |
|---|---|---|---|
| 1,811,159 | 6/1931 | Smalley | 432/48 |
| 2,606,372 | 8/1952 | Foulder et al. | 34/46 |
| 2,631,727 | 3/1953 | Cichelli | 210/31 R |
| 2,782,246 | 2/1957 | Evans | 236/15 BF |
| 3,010,657 | 11/1961 | Post | 432/48 |
| 3,624,917 | 12/1971 | Moore | 34/46 |
| 4,050,911 | 9/1977 | Welsh | 55/197 |

Primary Examiner—John J. Camby
Attorney, Agent, or Firm—Salvatore A. Giarrantana; Francis L. Masselle; Edwin T. Grimes

[57] ABSTRACT

A cooling vent within a thermal system, which has heat otherwise supplied to regulate the temperature thereof, is controlled to open and close incrementally so that temperature control near room ambient is facilitated.

9 Claims, 5 Drawing Figures

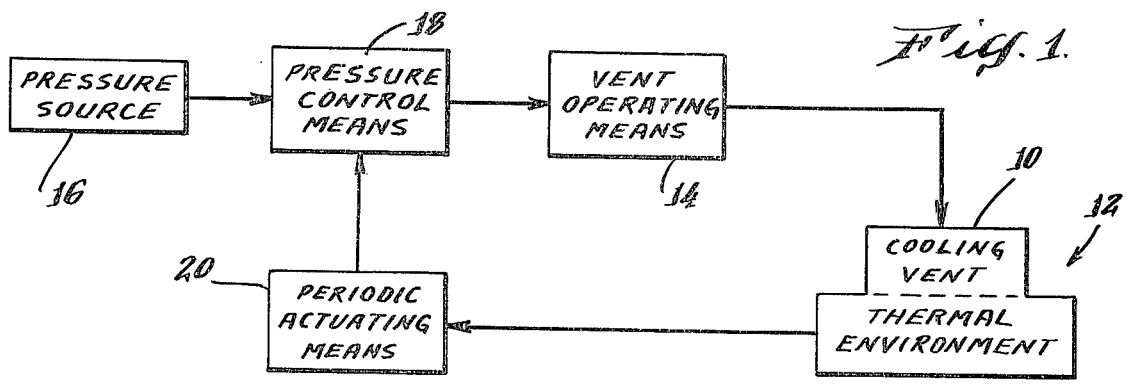
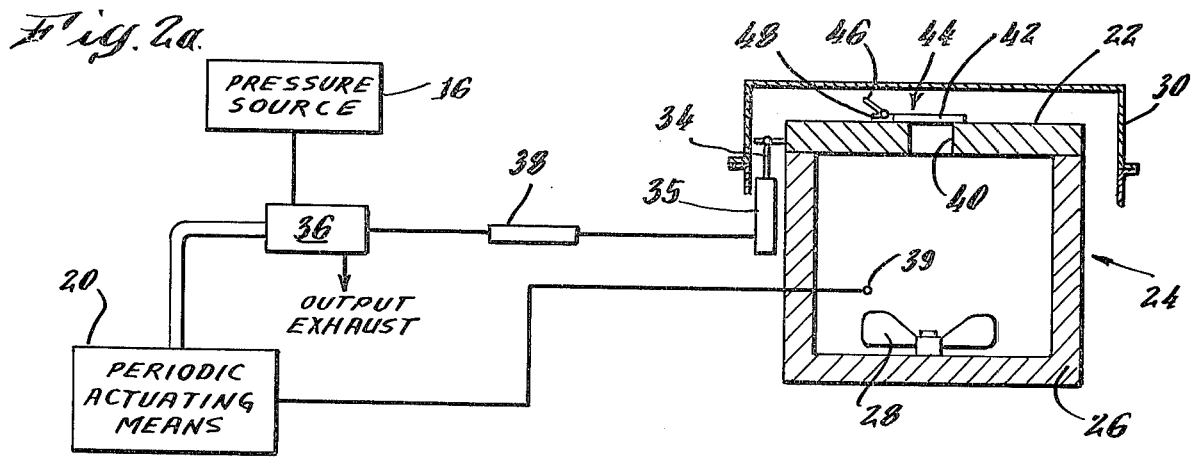
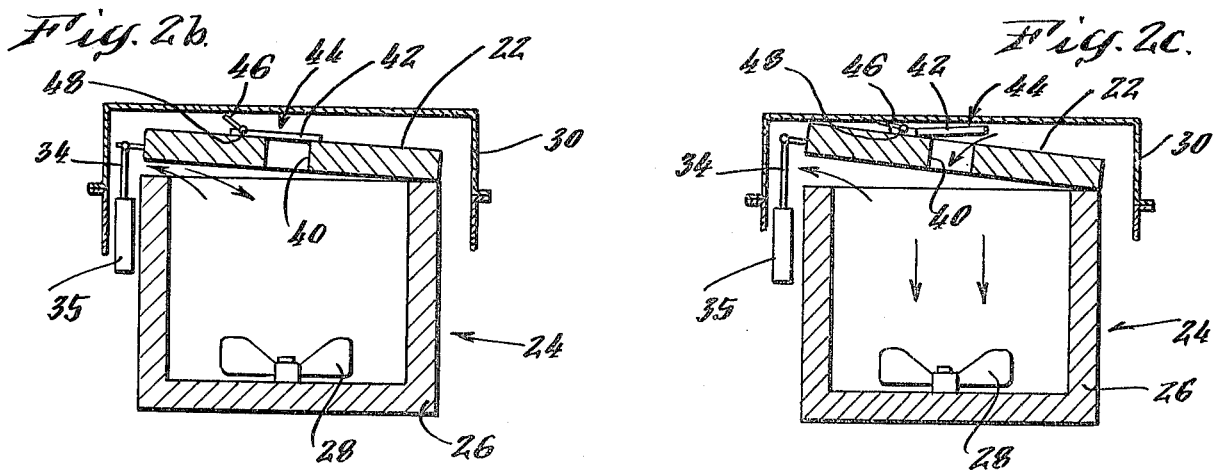
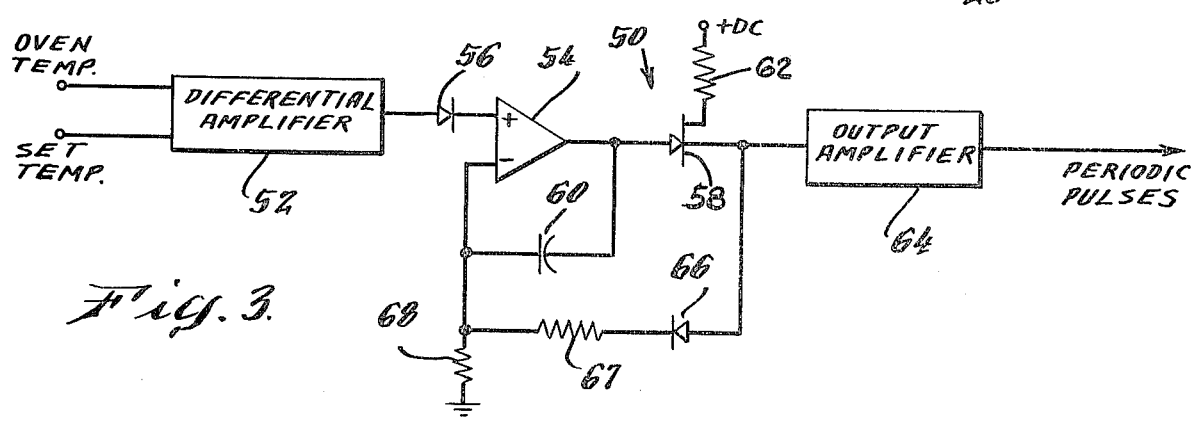

VENT CONTROL FOR A THERMAL SYSTEM

BACKGROUND OF THE INVENTION

The present invention relates to temperature control apparatus wherein a cooling vent is operated incrementally and heat is otherwise supplied to facilitate temperature regulation near room ambient conditions. Such apparatus is commonly known but in the prior art apparatus, the cooling vent is only operated to be closed or fully opened and therefore, temperature regulation becomes difficult near room ambient set points because fluctuations commonly occur about the set point when increased heat loss is required to maintain control and considerable thermal gradients occur within the thermal system. Consequently, control response is slow and heat is supplied while the thermal system is below the temperature set point during each cycle of fluctuation, which are both undesirable for many obvious reasons to those skilled in the art of thermal systems.

SUMMARY OF THE INVENTION

It is the object of this invention to incrementally operate a cooling vent in a thermal system for improved temperature control near room ambient.

It is another object of this invention to further enhance control by providing a two stage vent which brings cool air into the thermal system through one stage and exhausts hot air therefrom through the other stage.

These objects are accomplished according to one embodiment of the present invention by operating the cooling vent with a pneumatic cylinder to which pressure is controlled by a solenoid valve that is periodically actuated to incrementally open and close the vent in accordance with the temperature variation from set point. In other embodiments, the solenoid valve is actuated by a fixed duration pulse of which the period is derived by integrating a signal representative of the temperature error and a controlled opening is disposed through an oven top which is also lifted to provide the two stage vent.

BRIEF DESCRIPTION OF THE DRAWINGS

The manner in which these and other objects of the present invention are achieved will be understood from the following description, the appended claims, and the attached drawings wherein:

FIG. 1 is a block diagram of a thermal system which includes the cooling vent control apparatus of this invention;

FIGS. 2a, 2b, 2c relate to one embodiment of the invention wherein the top of an oven within a gas chromatograph is opened as the cooling vent;

FIG. 3 is a combined schematic and block diagram of the periodic actuating means that is utilized in the FIG. 2 embodiment of the invention.

DESCRIPTION OF THE PREFERRED EMBODIMENT

Turning now to the drawings, the cooling vent control apparatus of this invention is incorporated within the block diagram of FIG. 1 where an otherwise conventional cooling vent 10 is included as part of a thermal system 12 to which heat is also supplied as necessary to regulate the temperature thereof. Pressure actuated means 14 for operating the cooling vent 10 is connected thereto, while a source 16 of pressure is connected to the vent operating means 14 through a means 18 for controlling the output from the pressure source 16. A means for periodically actuating the pressue control means 18 is disposed between the thermal system 12 and the pressure control means 18 to pressurize and depressurize the vent operating means 14 in accordance with the temperature variation from set point. Of course, the physical nature of the thermal system 12 and the flow capacity of the cooling vent 10 all affect the results that are attained in maintaining temperature control of the thermal system 12. Furthermore, such results will also depend on the frequency of the periodic actuating means 20 and whether the vent operating means 14 is pressurized or depressurized for the full actuation periods.

An appropriate application for the apparatus of this invention is found in a gas chromatograph which characteristically includes a tubular column that is disposed within an oven. The column temperature is controlled throughout analysis and therefore, a vent exists in most gas chromatographs to provide the additional heat loss necessary for maintaining control near room ambient temperature where the heat losses of the oven are very low. Usually an exterior wall is simply opened as the vent to admit room ambient air until the control temperature is reached, however, the difficulties discussed previously in the Background Of Invention are commonly encountered with gas chromatographs of this type. The apparatus of this invention has been incorporated to operate an oven top 22 in a gas chromatograph 24 of this type as illustrated in FIG. 2a.

Of course, the oven top 22 and all of the other oven walls are insulted and a fan 28 is disposed therein to provide air circulation. Otherwise, the gas chromatograph 24 is disposed within an outer container 30 and the vent operating means 14 in this embodiment is a pneumatic cylinder 35 with a movable piston 34 that is connected to the oven top 22. A solenoid valve 36 serves as the pressure control means 18 and applies pneumatic pressure from the source 16 to the cylinder 35 through a restrictor 38 which presents a flow impedance. The periodic actuating means 20 directs electrical signals to the solenoid valve 36 from which the output is opened to exhaust when the pressure source 16 is shut off thereby. Otherwise, the periodic actuating means 20 is also connected to the oven 26 to monitor the actual temperature therein, such as with a thermocouple 39.

When temperature control requires that the oven 26 heat losses be increased, the periodic actuating means 20 causes the solenoid valve 36 to pressurize the cylinder 35 through the flow restrictor 38 for one operating increment. In the manner shown by FIG. 2b, the piston 34 of the cylinder 35 will move through a distance to lift the oven top 22 by some amount during this operating increment. If the temperature set point is not reached during the first operating increment, the periodic actuating means 20 again causes the solenoid valve 36 to pressurize the cylinder 35 through the flow restrictor 38 for another operating increment. The cylinder 35 continues to be pressurized thereafter during each operating increment so maintaining the temperature very close to the set point. Then during the next operating increment, the periodic actuating means 20 causes the pressure source 16 to be shut off by the solenoid valve 36 and therefore, the cylinder 35 is depressurized through the low restrictor 38 and the output of the solenoid valve 36 which is then opened to exhaust. Of course, the piston 34 of the cylinder 35 will be retracted through a distance to lower the oven top 22 by some amount during this operating increment. So long as the oven 26 remains at or just below the temperature set point thereafter, the periodic actuating means 20 causes the pressure source 16 to be shut off by the solenoid valve 36 during each operating increment, with the cylinder 35 being depressurized during each such increment. If the temperature does not return above the temperature set point, the oven top 22 will completely close. Typically, the oven top 22 is lifted incrementally to a mean opening point about which it is lifted and dropped in successive increments so maintaining the set temperature. Therefore, stabilization of the oven 26 at the temperature set point is attained with the minimum average oven top opening necessary to give sufficient heat loss from the oven to allow control of the temperature at the set point. By having the minimum vent opening the temperature gradients and fluctuations in the oven are minimized. Of course, the distance traveled throughout each operating increment by the oven top 22 depends on the impedance of the flow restrictor 38 and the bore volume of the cylinder 35, so that this distance can be readily adjusted to meet the requirements of any thermal system by merely changing the impedance of the flow restrictor 38 or the pressure of the source 16.

Although the oven top opening shown in FIG. 2b is advantageous under some control conditions because cool air entering the oven 26 is mixed with hot air exhausting therefrom to provide a more homogeneous environment therein, the flow of cooling air should not be impeded in this way, when the temperature set point is very close to that of room ambient. To provide this greater flow of cooling air, an opening 40 is disposed in line with the low pressure region of the fan 28 and a cover plate 42 is disposed thereover to seal off the over 26. Also, means 44 for displacing the plate 42 from over the opening 40 in operable sequence with the cylinder 35 is included in this improved embodiment of the invention. A trigger lever 46 is affixed to the plate 42 and both are pivotally affixed to the oven top 22 by a hinge pin 48, as the plate displacement means 44 in this embodiment.

When the temperature set point is very close to that of room ambient, the cylinder 35 operates to lift the oven top 22 to the position shown in FIG. 2b as discussed previously, at which time the trigger lever 46 of this embodiment initially contacts the container 30 of the gas chromatograph 24. As the oven top 22 continues to rise thereafter, the cover plate 42 is displaced to uncover the opening 40 therethrough as shown in FIG. 2c where arrows are utilized to illustrate the air flow pattern that then exists through the oven 26. Due to the low pressure region of the fan 28, cool air is taken in through the opening 40, while hot air is exhausted from the oven 26 through the opening that is developed by lifting the oven top 22 and a greater amount of cooling air is admitted than by the single air flow opening shown in FIG. 2b. From the time that the trigger lever 46 initially contacts the container 30 the amount of cover plate displacement from over the opening 40 is proportional to the distance through which the oven top 22 is raised by the cylinder 35 and therefore, the cover plate 42 is operable in sequence with the cylinder 35 between its closed positioned of FIG. 2b and its fully open position of FIG. 2c.

Although many circuit arrangements are possible for the periodic actuating means 20, the circuit utilized in the embodiment of FIG. 2a is illustrated in FIG. 3 wherein a means 50 for generating a pulse of fixed duration is included. The temperature error signal between the actual oven temperature and the set point is derived through a differential amplifier 52 of conventional construction and is connected to the noninverting input of an operational amplifier 54 through a forward biased diode 56. Output from the operational amplifier 54 is connected to both the emitter of a unijunction transistor 58 and its own inverting input through a capacitor 60. One base of the unijunction transistor 58 is positively biasedthrough a resistor 62, while the other base of the unijunction transistor 58 is connected to both the input of an output amplifier 64 and the inverting input of the operational amplifier 54 through a reverse biased diode 67 and a resistor 67. The inverting input of th operational amplifier 54 is also grounded through a resistor 68.

Those skilled in the electrical arts will readily understand that operational amplifier 54 is arranged to integrate whatever signal is presented at the noninverting input thereof. Of course, only positive temperature error signals are presented due to the diode 56 and in this embodiment, the differential amplifier 52 is arranged to produce a positive output whenever the oven temperature is above the set point. The unijunction transistor 58 in the pulse generating means 50 is only conductive when output from the operational amplifier 54 attains a greater positive voltage level than the bias level connected to the resistor 62 and consequently, pulses are only initiated when the temperature error signal has been integrated for whatever time duration is necessary to reach this level. The output amplifier 64 then produces a pulse having a duration equal to the conductive period of the unijunction transistor 58 which is the time required for the capacitor 60 to be discharged by output from the unijunction transistor 58 through resistor 67. Of course, the time duration of the pulse from output amplifier 64 can be varied merely by changing the value of resistor 67 and in the embodiment of FIG. 2a, this time duration was fixed at one second, while the flow impedance of restrictor 38 was chosen to provide full stroke of the piston 34 over 45 seconds to open the vent and 60 seconds to close it.

Although this invention has been disclosed herein by describing only a few embodiment thereof, it should be understood by those skilled in the art that numerous changes in the details of construction and the combination or arrangement of parts could be made in the described embodiments without departure from the true scope and spirit of the invention. Therefore, the present disclosure should be construed as illustrative rather than limiting.

What I claim is:

1. Apparatus for controlling a cooling vent in a thermal system wherein heat is otherwise supplied to control the temperature thereof at a set point, said apparatus comprising:

pressure actuated means for operating the cooling vent;

a source of pressure;

means for controlling output from said pressure source; and means for periodically actuating said pressure control means to pressurize and depressurize said vent operating means in attaining the minimum average vent opening necessary to maintain temperature control of the thermal system at the set point;

and wherein the thermal system is the oven of a gas chromatograph and the cooling vent is the top of the oven which is positionable to admit room ambient air, said operating means being a pneumatic cylinder having a piston that is connected to the oven top and said pressure control means being a solenoid valve that is electrically driven from said periodic actuating means; and a fan disposed within the oven and the oven top including an opening therethrough aligned with the low pressure region of said fan; and a plate disposed to cover said opening, a means for displacing said plate from over said opening in operable sequence with said pneumatic cylinder, said pneumatic cylinder lifting the oven top to a predetermined position during this operation with air being exchanged between the oven and room ambient through a common opening, after which said plate displacement means becomes operable together with said pneumatic cylinder and air then being taken in through the opening in the oven top and exhausted through the opening between the oven and the oven top.

2. Apparatus for controlling the cooling of an oven of a gas chromatograph wherein heat is otherwise supplied to control the temperature thereof at a set point, said apparatus comprising:

said oven having a displaceable oven wall;

means for displacing said displaceable oven wall to form a first air passage between room ambient and the interior of the oven;

means for periodically actuating said means for displacing said displaceable oven wall to obtain the minimum average first air passage area necessary to maintain the temperature in the oven at the set point;

said oven wall having an opening therethrough to form a second air passage between the room ambient and the interior of the oven, a cover plate disposed to cover said opening, means for displacing said cover plate from over said opening in operable sequence with said means for displacing said displaceable oven wall so that when said oven wall is in a first position, air is exchanged between the oven and room ambient only through said first air passage when said oven wall is in a second position air is taken in from the room ambient through said second air passage and exhausted from the interior of the oven through said first air passage.

3. Apparatus according to claim 2 further comprising a fan disposed within the oven having a low pressure region aligned with said opening in the displaceable oven wall.

4. Apparatus according to claim 2 wherein said displaceable oven wall is in the oven top.

5. Apparatus according to claim 4 wherein said means for displacing said displaceable oven wall to form the first air passage comprises a pneumatic cylinder having a piston that is connected to the oven top, control means for said piston including a solenoid valve that is electrically driven from said periodic actuating means;

said periodic actuating means including means for generating a pulse of fixed duration at a varying frequency with the period thereof being inversely proportional to the average difference existing between the oven temperature and the cooling point.

6. Apparatus according to claim 5 wherein said pulse generating means includes an operational amplifier having the inverting input thereof grounded through a first resistor and connected through a capacitor to the output thereof while an error signal of the difference between the oven temperature and the set point is derived through a differential amplifier and is connected to the noninverting input thereof, the output of said operational amplifier also being connected to the emitter of a unijunction transistor with the first base thereof being connected to an output amplifier, the inverting input of said operational amplifier also being connected to said first base through a second resistor while a second base of said unijunction transistor is positively biased through a third resistor, said error signal being integrated by said operational amplifier until the biased level on said second base is reached to render said output amplifier conductive for a duration equal to the time required to discharge said capacitor through said second transistor.

7. Apparatus for controlling the cooling of an oven of a gas chromatograph wherein heat is otherwise supplied to control the temperature thereof at a set point, said apparatus comprising:

an oven top pivotally connected to the oven along one edge thereof;

means for pivotally displacing said oven top to form a first air passage between room ambient and the interior of the oven;

means for periodically actuating said means for displacing said oven top to obtain the minimum average first air passage area necessary to maintain the temperature in the oven at the set point;

said oven top having an opening therethrough to form a second air passage between the room ambient and the interior of the oven, a cover plate disposed to cover said opening;

an outer container encompassing the upper portion of said oven in spaced relationship with respect thereto;

trigger means interposed between said outer container and said oven top for displacing said cover plate from over said opening in operable sequence with said means for displacing said oven top.

8. Apparatus according to claim 7 wherein said trigger means for displacing said cover plate from over said opening in operable sequence with said means for displacing said oven top, is mounted so that when said oven top is in a first position, air is exchanged between the oven and room ambient only through said first air passageway and when said oven top is in a second position, air is taken in from room ambient through said second air passage and exhausted from said oven through said first air passage.

9. Apparatus according to claim 7 wherein said trigger means includes a trigger level affixed to said cover plate, said trigger lever and said cover plate being pivotally affixed to the oven top so that when said oven top is pivoted upwardly, said trigger lever engages said outer container to pivot said cover plate to its open position.

* * * * *

UNITED STATES PATENT AND TRADEMARK OFFICE
CERTIFICATE OF CORRECTION

PATENT NO. : 4,111,643

DATED : September 5, 1978

INVENTOR(S) : John M. Welland

It is certified that error appears in the above–identified patent and that said Letters Patent are hereby corrected as shown below:

Column 1, line 60, change "EMBODIMENT" to --EMBODIMENTS--

Column 2, line 3, change "pressue" to --pressure--

Column 2, line 67, change "low" to --flow--

Column 4, line 14, change "biasedthrough" to --biased through--

Column 4, line 18, change "th" to --the--

Column 6, line 60, change "level" to --lever--

Signed and Sealed this

Eighth Day of January 1980

[SEAL]

Attest:

SIDNEY A. DIAMOND

Attesting Officer     Commissioner of Patents and Trademarks